United States Patent
Esposito et al.

[11] Patent Number: 6,044,971
[45] Date of Patent: Apr. 4, 2000

[54] CLIP CARTRIDGE

[75] Inventors: Felix F. Esposito, Stratford; Lawrence M. Rank, Monroe, both of Conn.; Lawrence Crainich, Charlestown; Paul A. LaRue, Chesterfield, both of N.H.

[73] Assignee: United States Surgical Corporation, Norwalk, Conn.

[21] Appl. No.: 09/013,822

[22] Filed: Jan. 27, 1998

Related U.S. Application Data

[63] Continuation-in-part of application No. 08/948,468, Oct. 10, 1997, abandoned.

[51] Int. Cl.[7] ............................................. B65D 85/24
[52] U.S. Cl. ................................... 206/339; 206/340
[58] Field of Search ............................ 206/338, 339–341, 206/376–378, 504, 560; 606/157

[56] References Cited

U.S. PATENT DOCUMENTS

| | | |
|---|---|---|
| 3,270,745 | 9/1966 | Wood . |
| 3,326,216 | 6/1967 | Wood . |
| 3,351,191 | 11/1967 | Mallina . |
| 3,363,628 | 1/1968 | Wood . |
| 3,604,561 | 9/1971 | Mallina . |
| 3,631,707 | 1/1972 | Miller . |
| 3,713,533 | 1/1973 | Reimels . |
| 3,867,944 | 2/1975 | Samuels . |
| 4,076,120 | 2/1978 | Carroll et al. . |
| 4,146,130 | 3/1979 | Samuels et al. . |
| 4,211,351 | 7/1980 | Monacelli . |
| 4,212,390 | 7/1980 | Raczkowski et al. . |
| 4,294,355 | 10/1981 | Jewusiak et al. . |
| 4,344,531 | 8/1982 | Giersch . |
| 4,361,229 | 11/1982 | Mericle . |
| 4,397,312 | 8/1983 | Molko . |
| 4,412,617 | 11/1983 | Cerwin . |
| 4,485,953 | 12/1984 | Rothfuss . |
| 4,685,564 | 8/1987 | Hills et al. . |
| 4,696,396 | 9/1987 | Samuels . |
| 4,799,481 | 1/1989 | Transue et al. . |
| 4,936,447 | 6/1990 | Peiffer . |
| 4,961,499 | 10/1990 | Kulp . |
| 4,971,198 | 11/1990 | Mericle . |
| 4,972,949 | 11/1990 | Peiffer . |
| 5,040,676 | 8/1991 | Bell . |
| 5,046,611 | 9/1991 | Oh . |
| 5,083,664 | 1/1992 | Feng ........................................ 206/376 |
| 5,199,566 | 4/1993 | Ortiz et al. . |
| 5,201,416 | 4/1993 | Taylor . |
| 5,279,416 | 1/1994 | Malec et al. . |
| 5,358,692 | 10/1994 | Reynolds ............................... 206/560 |
| 5,544,747 | 8/1996 | Horn ..................................... 206/378 |
| 5,645,177 | 7/1997 | Lin ........................................ 206/378 |
| 5,733,293 | 3/1998 | Scirica et al. .......................... 206/339 |
| 5,788,303 | 8/1998 | Chia-Hsiang ........................... 206/504 |
| 5,855,285 | 1/1999 | Laird et al. ............................. 206/378 |
| 5,908,430 | 6/1999 | Appleby ................................. 206/339 |

FOREIGN PATENT DOCUMENTS

| | | |
|---|---|---|
| 0 583 151 | of 1994 | European Pat. Off. . |
| 297 05 944 U | of 1997 | Germany . |

OTHER PUBLICATIONS

Horizon Surgical, An Advanced Ligating and Marking Clip System.

*Primary Examiner*—Paul T. Sewell
*Assistant Examiner*—Luan K. Bui
*Attorney, Agent, or Firm*—Dilworth & Barrese

[57] ABSTRACT

A clip cartridge for supporting a plurality of clips is provided. The clip cartridge includes a body defining a plurality of clip chambers each configured and dimensioned to receive a clip therein. Interlocking structure is provided on each end of the cartridge to facilitate attachment of a multiplicity of clip cartridges together. Clip cartridges housing different size clips have substantially identical external dimensions and internal dimensions which accommodate for the different size clips. The uniformity of the external dimensions of the cartridges housing different size clips facilitates attachment of the cartridges housing different size clips.

13 Claims, 11 Drawing Sheets

CLIP CARTRIDGE

This application is a continuation-in-part of Ser. No. 08/948,468 filed Oct. 10, 1997, now abandoned.

BACKGROUND

1. Technical Field

The present disclosure relates generally to a clip cartridge for supporting hemostatic clips, and more particularly to a clip cartridge having a plurality of spaced compartments, each configured to retain a single clip therein.

2. Background of Related Art

Clip cartridges for supporting hemostatic clips until they are needed for use are well known in the art. Typically, clip cartridges include a plurality of spaced vertical walls which project upwardly from a base member and define a plurality of compartments. Each compartment is dimensioned to support a clip therein and to receive the distal end of a clip applicator. Structure is also provided in each compartment to retain a clip within the compartment until needed for use. The retaining structure must permit easy access of a clip applicator into each compartment and easy removal of a clip and clip applicator from the compartment, while providing effective retention of a clip within the compartment.

U.S. Pat. No. 4,696,396 ("Samuels") discloses a hemostatic clip cartridge having a plurality of wall dividers that define individual clip compartments. Each compartment includes a central post for supporting a clip thereon. Each wall divider forms a compartment wall for two adjacent clip compartments. A pair of channel members are located on each compartment wall and extend into the compartment sufficiently to engage and retain a clip within the compartment.

U.S. Pat. No. 5,201,416 ("Taylor") discloses a hemostatic clip cartridge having a base portion and a body portion defining a plurality of clip retaining chambers. A hemostatic clip is supported on a central post positioned within each of the chambers. A pair of retaining means are positioned within each chamber above the top of the central post so as not to press directly inwardly on the clip. The retaining means narrows the distance between upper walls defining the chamber to retain a clip within the chamber. During removal of a clip from a respective chamber, the retaining means are deformed inwardly to facilitate removal of the clip from the chamber.

U.S. Pat. No. 4,961,499 ("Kulp") also discloses a hemostatic clip cartridge including a base and a plurality of spaced vertical walls which define a plurality of clip receiving slots. A clip receiving post is positioned within each slot to support a clip thereon. A retaining projection extends from each wall of each slot adjacent the upper end of the clip receiving post to secure the clip within a respective slot. The retaining projections each include a tapered clip engaging surface. During removal of a clip, the retaining projections move outwardly as a result of the camming action of the clip to facilitate removal of the clip from the slot.

During a surgical procedure, surgical instrumentation, i.e., needles, clips, cartridges, etc., must be strictly accounted for by surgical personnel to ensure that such instrumentation has not been inadvertently left within the patient during the surgical procedure. Clip cartridges, such as those discussed above, generally support between eight and ten clips. During surgical procedures which require the use of a large number of clips, i.e., greater than the number of clips supported in a single cartridge, or multiple size clips, the presence of a plurality of clip cartridges in the surgical area renders the surgical area more cluttered and increases the likelihood that surgical instrumentation will be left unaccounted for by the surgical personnel.

Accordingly, a need exists for an improved clip cartridge that can be easily manufactured, includes simplified clip retaining structure, and that can be easily accounted for during a surgical procedure.

SUMMARY

In accordance with the present disclosure, a clip cartridge is provided for supporting a plurality of clips therein. The clip cartridge is preferably molded and of monolithic construction and includes a body having a base and a plurality of upstanding walls. Adjacent upstanding walls define clip chambers which are configured and dimensioned to receive a clip therein. A pair of supporting members are positioned in each of the clip chambers to support a clip thereon. Each upstanding wall includes at least one stationary wall portion or at least one resilient wall portion. The upper end of each clip chamber is defined between a stationary wall portion and a resilient wall portion. A rigid projection is positioned on each stationary wall portion at a location opposite the resilient wall portion. During removal of a clip from a respective clip chamber, the rigid projection functions to cam the clip into engagement with the resilient wall portion to flex the resilient wall portion outwardly and facilitate removal of a clip from a clip chamber.

The body of the clip cartridge includes interlocking structure formed on each end thereof configured to engage similar interlocking structure formed on other like cartridges. The interlocking structure is preferably in the form of a dovetail recess formed on one end of the body and a dovetail projection formed on the other end of the body. The dovetail recess is configured to slidably receive the dovetail projection of like cartridges to attach two or more cartridges together. Moreover, the external dimensions of cartridges housing different size clips are substantially identical, thus permitting cartridges housing different size clips to be interlocked together.

In an alternate embodiment of the clip cartridge, each clip chamber is defined by a pair of stationary walls. A flexible projection is positioned on one of the stationary walls and extends into the clip chamber to retain a clip within the clip chamber. During removal of a clip from a respective clip chamber, the flexible projection is engaged by the clip and deformed to allow removal of the clip from the clip chamber.

BRIEF DESCRIPTION OF THE DRAWINGS

Various preferred embodiments are described herein with reference to the drawings, wherein.

DETAILED DESCRIPTION OF THE PREFERRED EMBODIMENTS

Preferred embodiments of the presently disclosed clip cartridge will now be described in detail with reference to the drawings, in which like reference numerals designate identical or corresponding elements in each of the several views.

Figure 1:
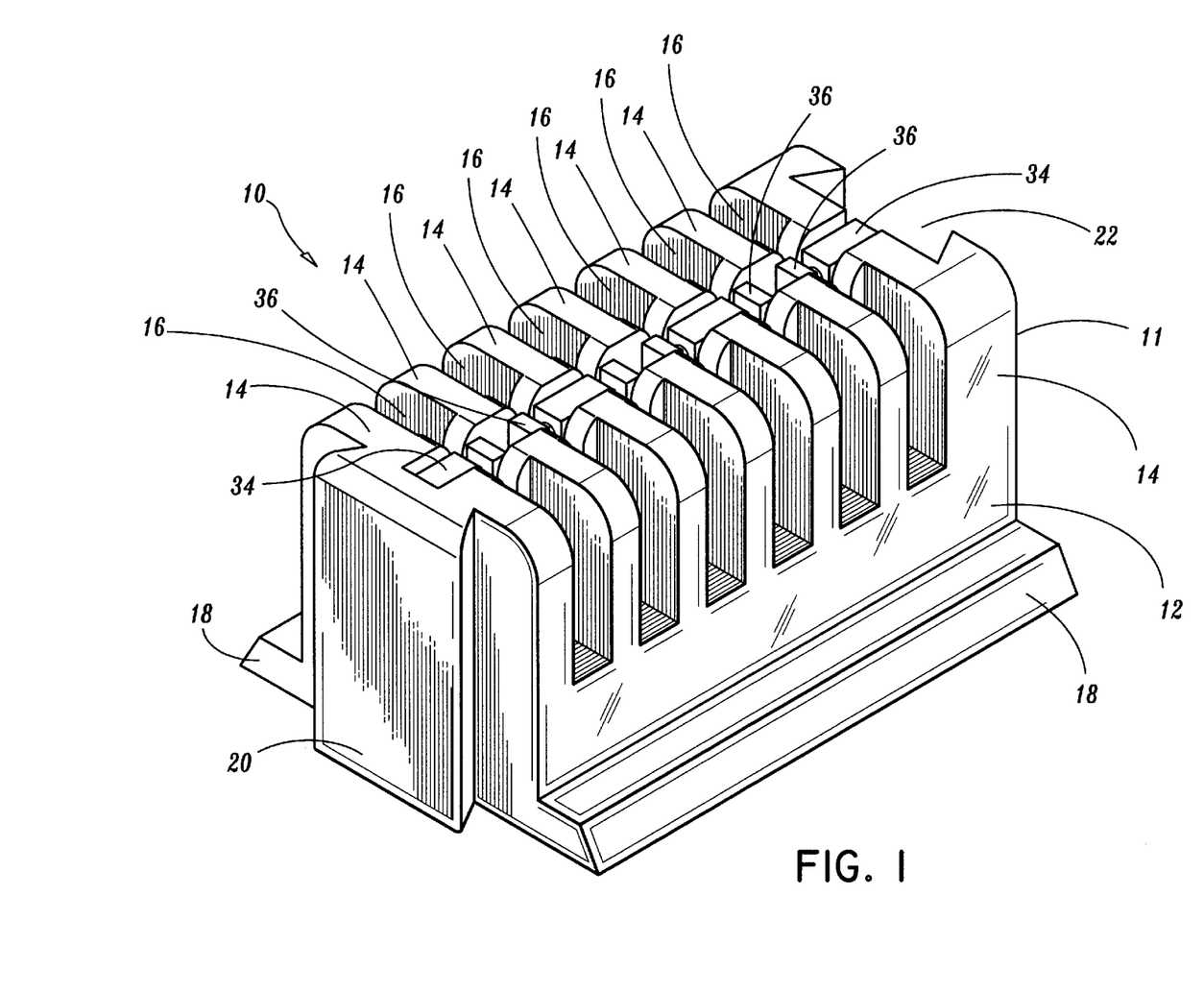
FIG. 1 is a perspective view of one embodiment of the clip cartridge.
Figure 2:
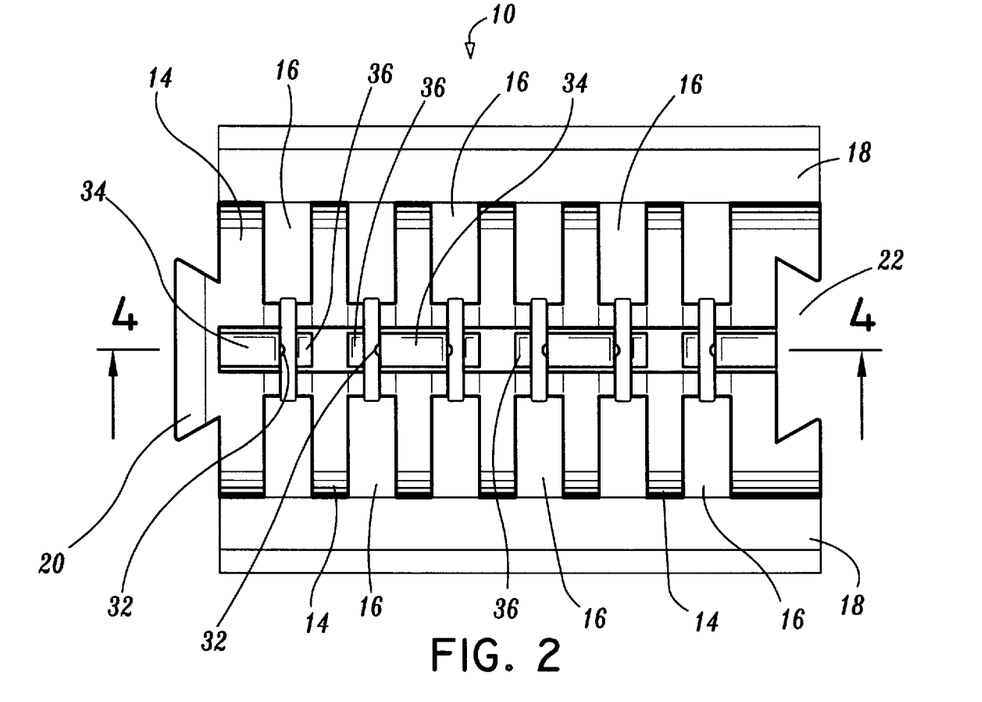
FIG. 2 is a top view of the clip cartridge shown in FIG. 1.
Figure 3:
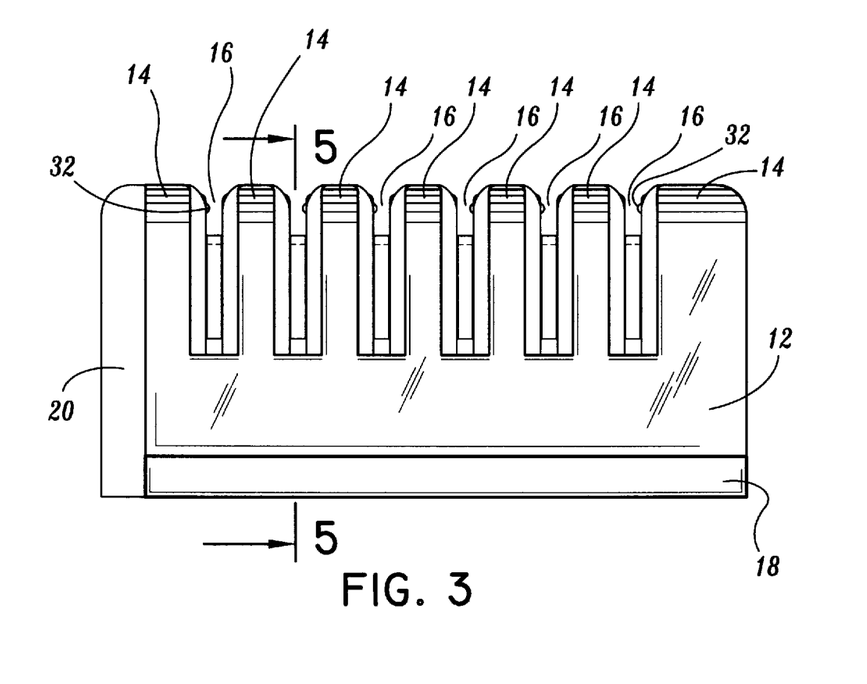
FIG. 3 is a side view of the clip cartridge shown in FIG. 1.

FIGS. 1–3 illustrate one embodiment of the clip cartridge shown generally as 10. Briefly, clip cartridge 10 includes a body 11 having a base 12 and a plurality of upstanding walls 14 that project upwardly from the base 12. Adjacent walls 14 define clip chambers 16. Although illustrated as having seven walls 14 defining six chambers, a greater or fewer number of walls are also envisioned. A base flange 18 is formed at the bottom of base 12 and will be described in greater detail below. A dovetail projection 20 and a dovetail recess 22 are positioned at opposite ends of clip cartridge 10. Dovetail projection 20 is configured and dimensioned to be received within a dovetail recess 22' of a second clip cartridge 10' (See FIGS. 7 and 8) as will be described below. The entire clip cartridge 10 can be molded in monolithic form. Alternately, clip cartridge 10 can be formed of multiple portions joined together using any known means, e.g., interlocking structure, sonic welding, etc. The cartridge is constructed of an engineering plastic or metal. Preferably a biocompatible plastic such as ABS material is used. In a preferred configuration, the material of construction is Dow Magnum from Dow Chemical available as code 2620 ABS.

Figure 4:
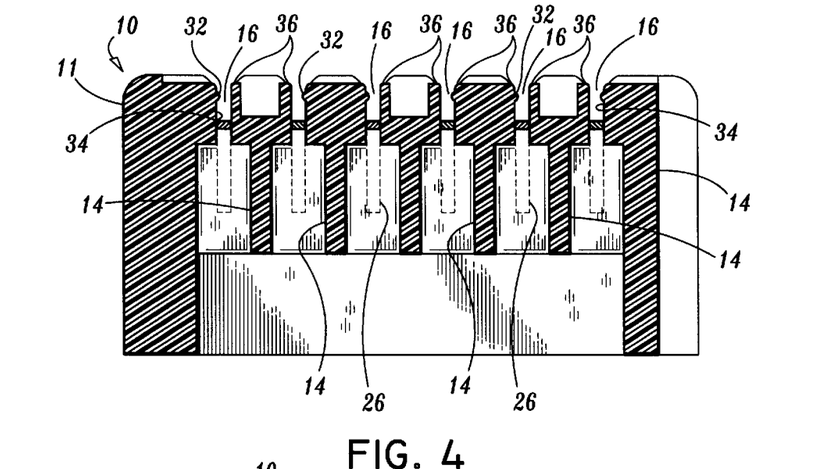
FIG. 4 is a cross-sectional view taken along section line 4—4 of FIG. 2.
Figure 5:
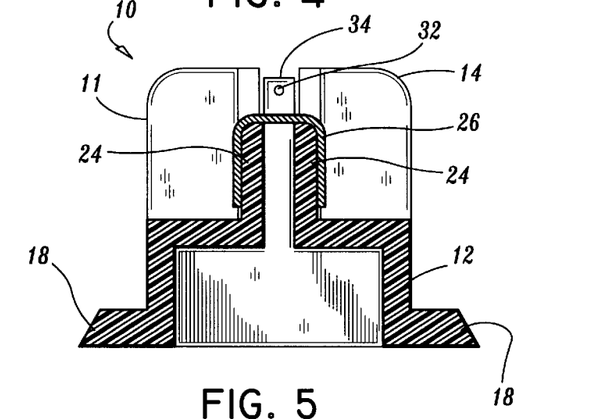
FIG. 5 is a cross-sectional view taken along section line 5—5 of FIG. 3.

Referring to FIGS. 4 and 5, each clip chamber 16 includes a pair of clip supporting or saddle members 24 configured to receive a clip 26 thereon. Clip saddle members 24 should extend to a height above base 12 greater than the length of legs 28 of clip 26 to provide space for a clip applicator (not shown) to engage the distal ends 30 of clip 26 during removal of clip 26 from clip cartridge 10. A rigid projection 32 extends into clip chamber 16 from a stationary section 34 of each upstanding wall 14 to prevent clip 26 from falling from a respective clip chamber 16. Projection 32 is spaced above saddle members 24 to allow the clip 26 to be loosely held within clip chamber 16. A resilient wall section 36 of upstanding wall 14 is positioned across from projection 32. The distance between the radially innermost surface of projection 32 and resilient wall section 36 is 0.004 of an inch smaller than the width of clip 26 plus or minus 0.003 of an inch.

Figure 6:
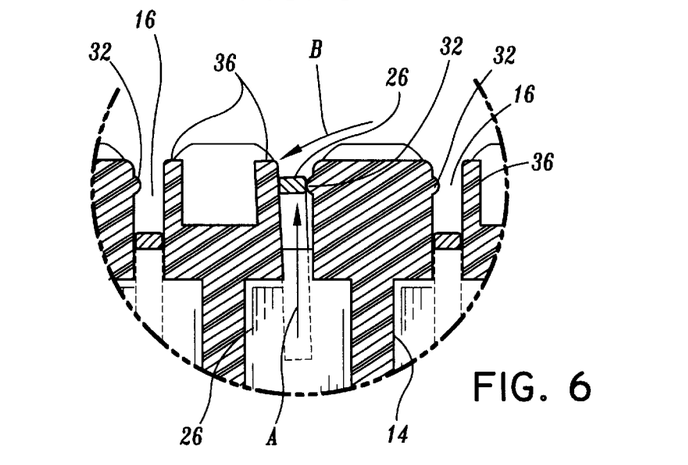
FIG. 6 is an enlarged side cross-sectional view of the clip chamber during removal of a clip therefrom.

Referring to FIG. 6, when a clip 26 is removed from clip chamber 16 in the direction indicated by arrow "A" by a clip applicator (not shown), the clip is cammed into resilient wall section 36 by rigid projection 32. Engagement between clip 26 and resilient wall section 36 causes resilient wall section 36 to bend outwardly in the direction indicated by arrow "B" to facilitate removal of clip 26 from clip chamber 16. It is also contemplated that the clip chamber be configured and dimensioned to provide a clearance between the clip and at least one wall section.

Figures 7, 8:
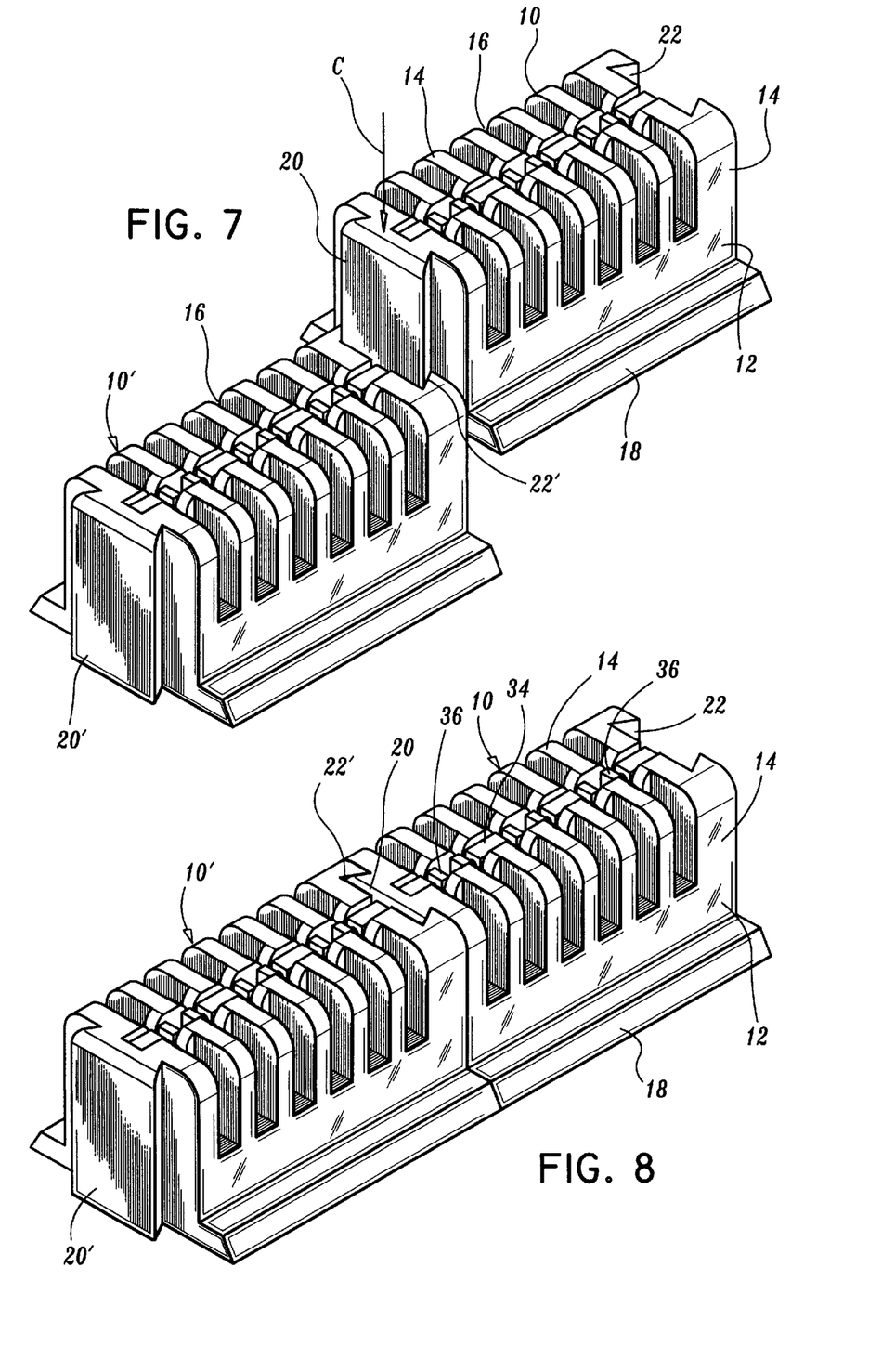
FIG. 7 is a side perspective view of two of the clip cartridges shown in FIG. 1 during attachment of the clip cartridges to each other.
FIG. 8 is a side perspective view of the clip cartridges shown in FIG. 7 in a fully attached position.

Referring to FIGS. 7 and 8, clip cartridge 10 includes a dovetail projection 20 on one end thereof and a dovetail recess 22 on the other end thereof. Dovetail projection 20 is dimensioned and configured to be received within the dovetail recess 22' of a second clip cartridge 10'. Dovetail projection 20 is slidable downwardly in the direction indicated by arrow "C" in FIG. 7 into dovetail recess 22' to attach two clip cartridges 10 and 10' together. A multiplicity of clip cartridges can be attached together to provide an integral clip cartridge assembly having the required number of clips for a surgical procedure. Although recess 22 and projection 20 are illustrated as being dovetail-shaped, other interlocking configurations are also envisioned.

Figure 9:
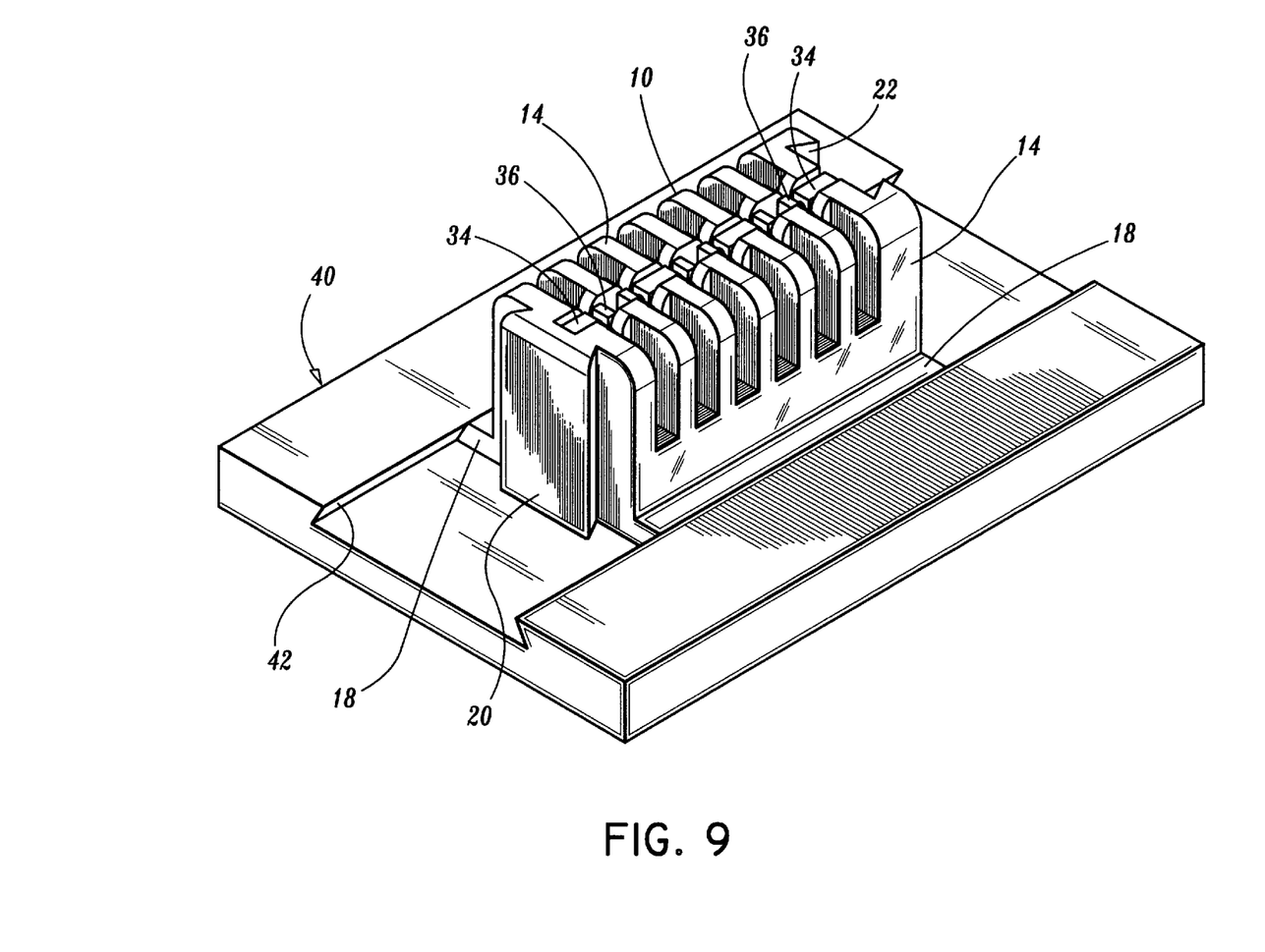
FIG. 9 is a perspective view of the clip cartridge shown in FIG. 1 secured to a weighted plate.

Referring to FIG. 9, a weighted plate 40 having an elongated slot 42 configured and dimensioned to receive base flange 18 of clip cartridge 10 may also be provided to secure clip cartridge 10 at a fixed location during a surgical procedure. Base flange 18 is slidable into slot 42 to secure clip cartridge 10 in place. Alternately, elongated slot 42 may be formed along the top surface of a surgical table (not shown) and cartridge 10 can be secured directly thereto. It is further contemplated that base flange 18 be provided with a plurality of slots in either parallel, box or other configuration.

Figure 10:
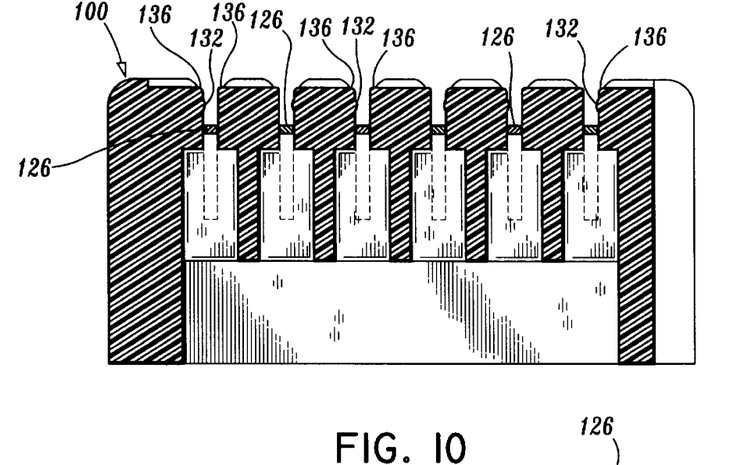
FIG. 10 is a side cross-sectional view of an alternate embodiment of the clip cartridge.
Figure 11:
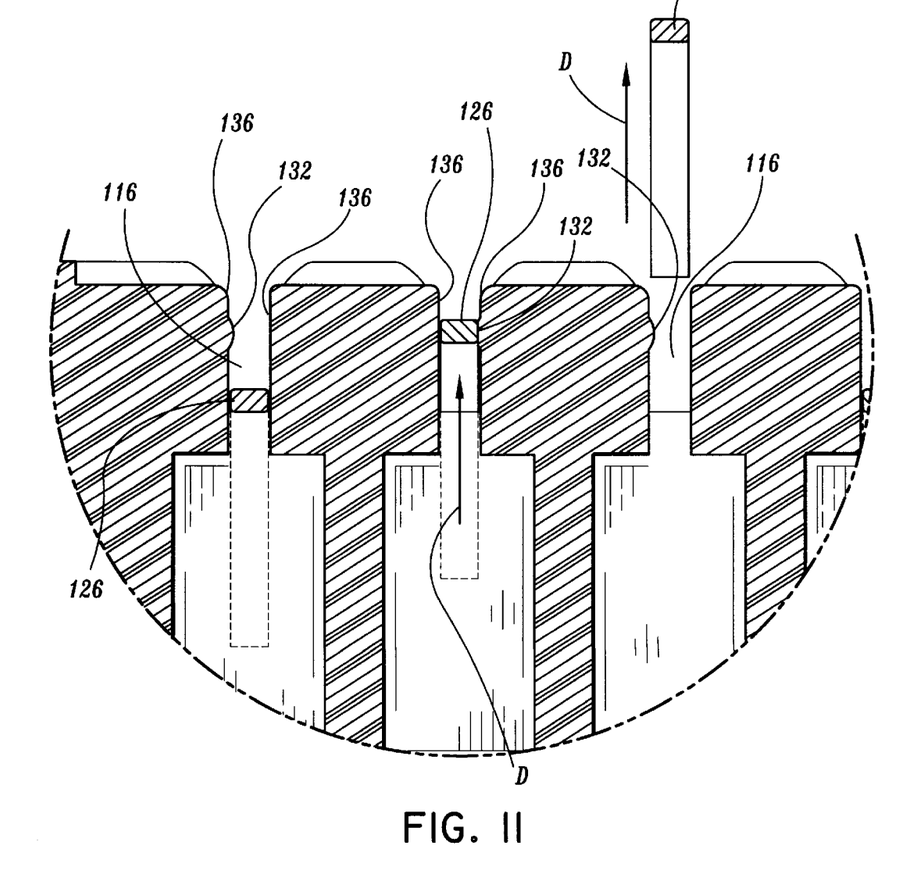
FIG. 11 is an enlarged side cross-sectional view of the clip chambers illustrating the clip in a supported position within the clip chamber, in a partially removed position, and in a fully removed position.
Figure 12:
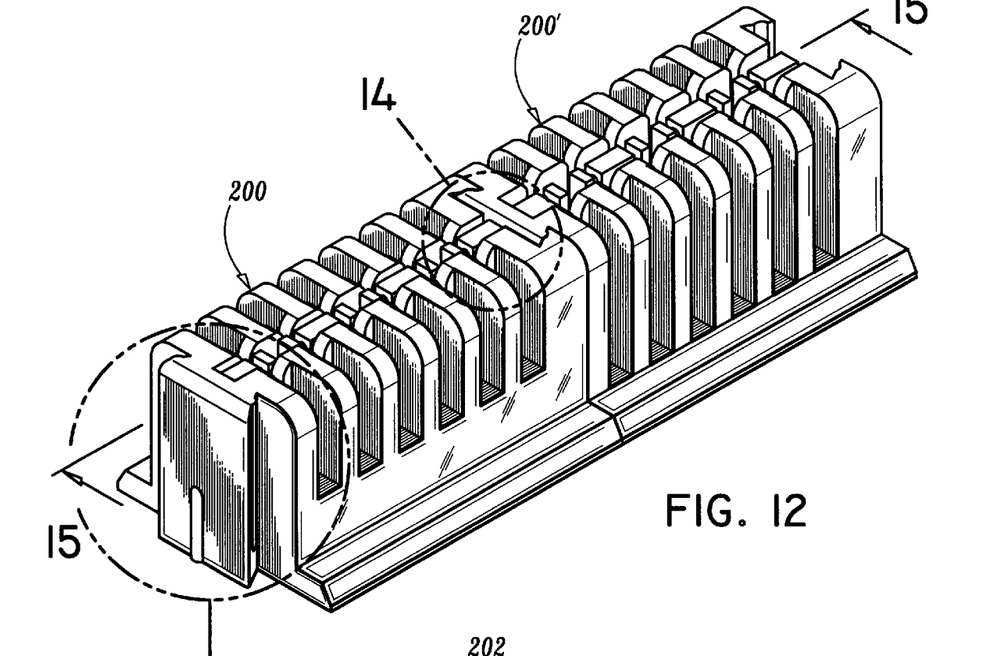
FIG. 12 is a perspective view of another alternate embodiment of the clip cartridge attached to a second clip cartridge.
Figure 13:
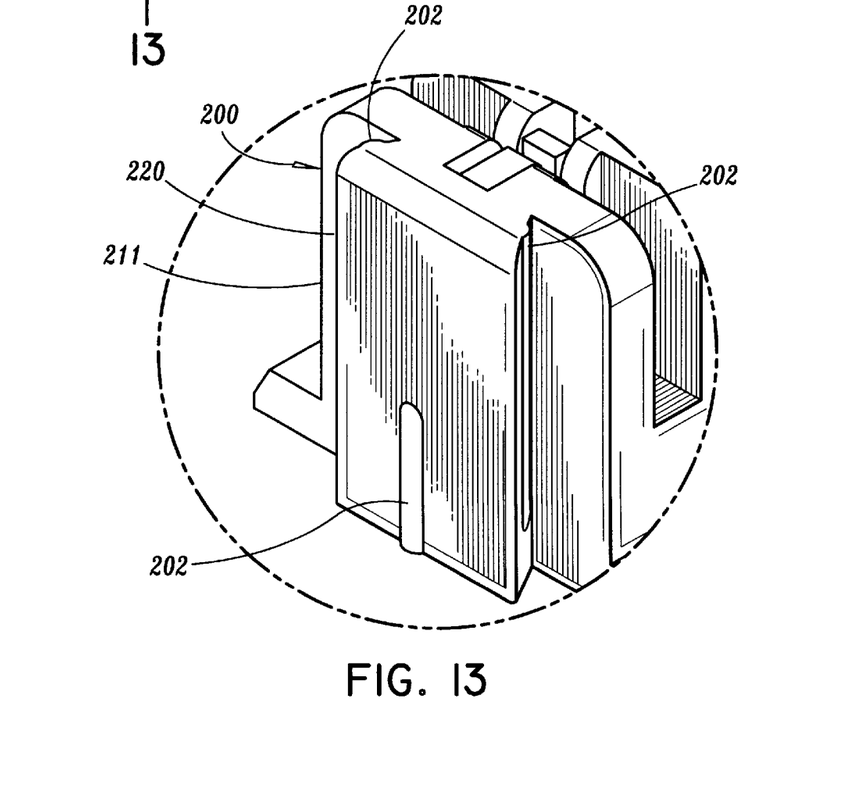
FIG. 13 is an enlarged perspective view of the area of detail indicated in FIG. 12.
Figure 14:
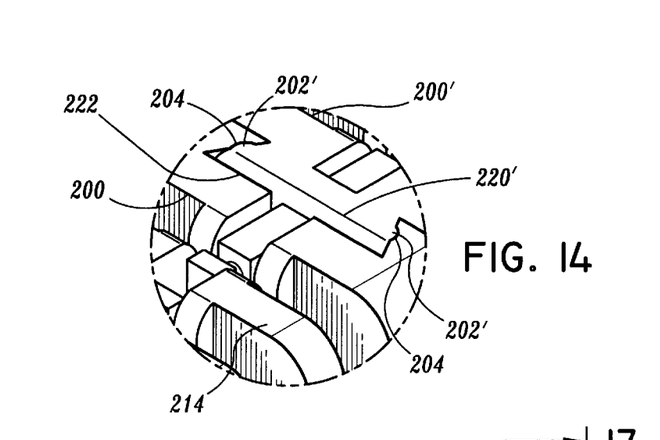
FIG. 14 is an enlarged perspective view of the interlocking structure of the clip cartridges shown in FIG. 12.

FIGS. 10 and 11 illustrate an alternate embodiment of the clip cartridge shown generally as 100. Clip cartridge 100 differs from clip cartridge 10 in that a resilient projection 132 has been provided on a stationary wall section 136 of clip cartridge 100 opposite a second stationary wall section. The distance between the radially innermost surface of projection 132 and the second stationary wall section 136 of clip cartridge 100 is preferably about 0.004 of an inch less than the width of clip 126. During removal of clip 126 from clip chamber 116 by a clip applicator (not shown), projection 132 is deformed by clip 126 as clip 126 is moved in the direction indicated by arrow "D" in FIG. 11 to facilitate removal of clip 126 from clip chamber 116. Alternately, projection 132 may be formed of a brittle material which is sheared off by clip 126 as the clip is removed from clip chamber 116 by a clip applicator.

FIGS. 12–17 illustrate another alternate embodiment of the clip cartridge, shown generally as 200. Clip cartridge 200 is attached to a second clip cartridge 200' using interlocking structure such as disclosed above in reference to clip cartridge 10. Clip cartridge 200 is substantially similar to clip cartridge 10 in most respects. However, clip cartridge 200 further includes retaining ribs 202 formed on dovetail projection 220 of cartridge body 211 and retaining grooves 204 formed along dovetail recess 222. Grooves 204 are positioned and dimensioned to receive retaining ribs 202' of a second cartridge, e.g., cartridge 200'. The rib/groove construction ensures a tight connection between adjacent cartridges and prevents relative movement therebetween.

Figure 15:
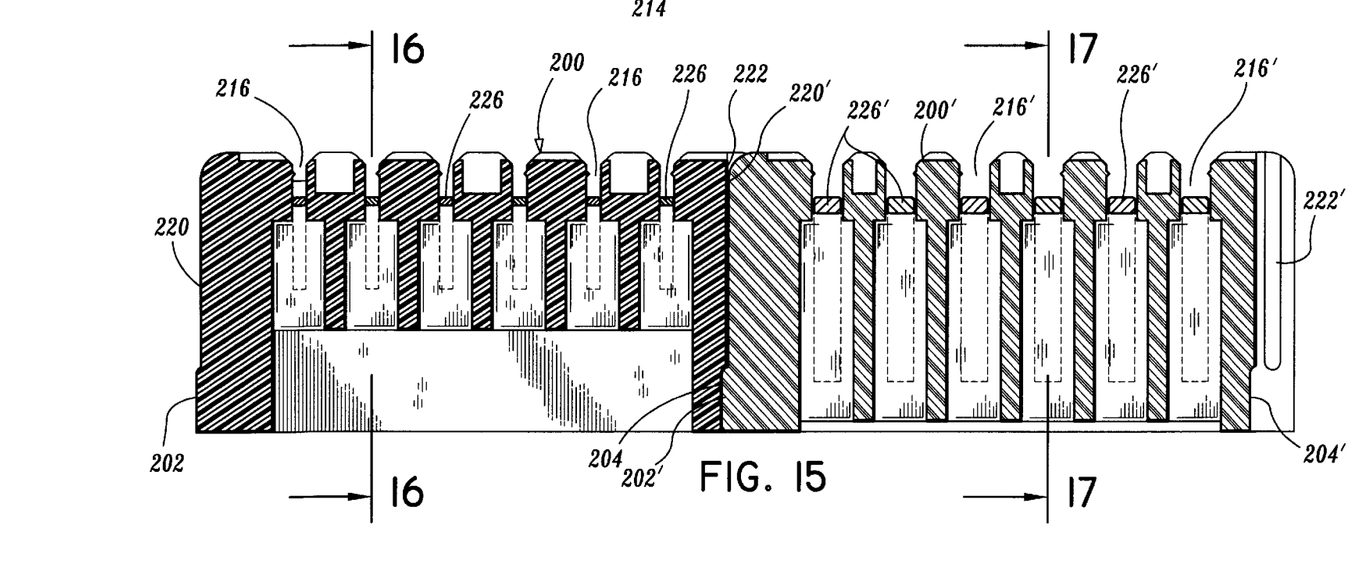
FIG. 15 is a side cross-sectional view taken along section line 15—15 of FIG. 12.
Figure 16:
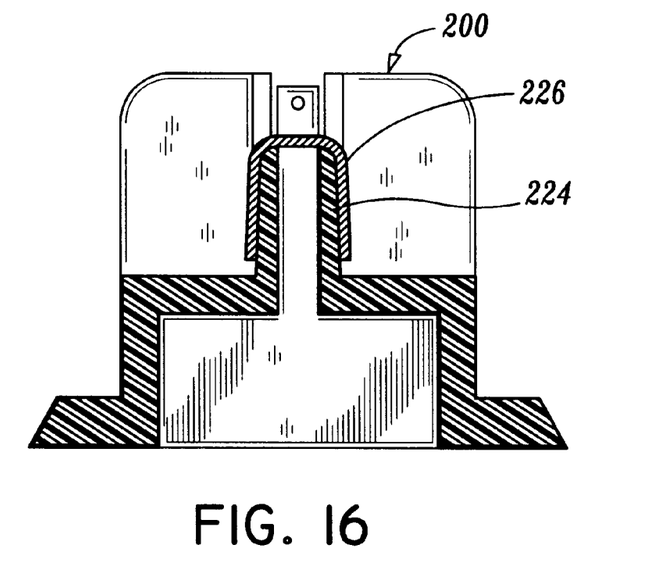
FIG. 16 is a cross-sectional view taken along section line 16—16 of FIG. 15.
Figure 17:
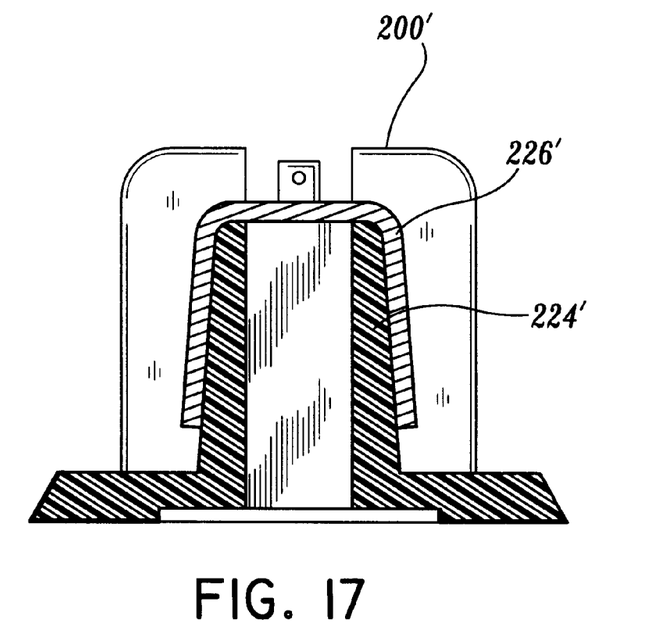
FIG. 17 is a cross-sectional view taken along section line 17—17 of FIG. 15.

Each of the cartridges 10, 100 and 200 disclosed above can be constructed to accommodate various size clips, e.g., small, medium, medium-large and large. For example, FIGS. 15–17 illustrate cross-sectional views of cartridges 200 and 200' for accommodating different size clips 226 and 226', respectively. Preferably, the external dimensions of these cartridges and other cartridges housing different size clips are substantially identical regardless of the size of the clips supported therein, i.e., each of the cartridges has substantially the same length, height and width as each of the other cartridges. The internal dimensions of the different clip chambers 216 are modified to accommodate the various size clips. For example, saddle members 224 and 224' formed in cartridges 200 and 200', respectively, can be dimensioned and configured to support a specific size clip. Further, the width of upstanding walls 214 and 214' can be varied to accommodate different size clips. Since the external dimensions of clip cartridges 200 and 200' are substantially the same, these cartridges may be connected together using the disclosed interlocking structure, e.g., dovetail projection 220' and dovetail recess 222.

It is also envisioned that each cartridge may be color-coded to identify the size of the clips supported within the cartridge. For example, blue cartridges may be used to identify cartridges carrying large clips, whereas red cartridges may be used to identify cartridges housing small clips. Alternately, other indicia may be used to identify the size of the clip housed within a respective cartridge, i.e., lettering, numbering, tactile indicators, etc.

Figure 18:
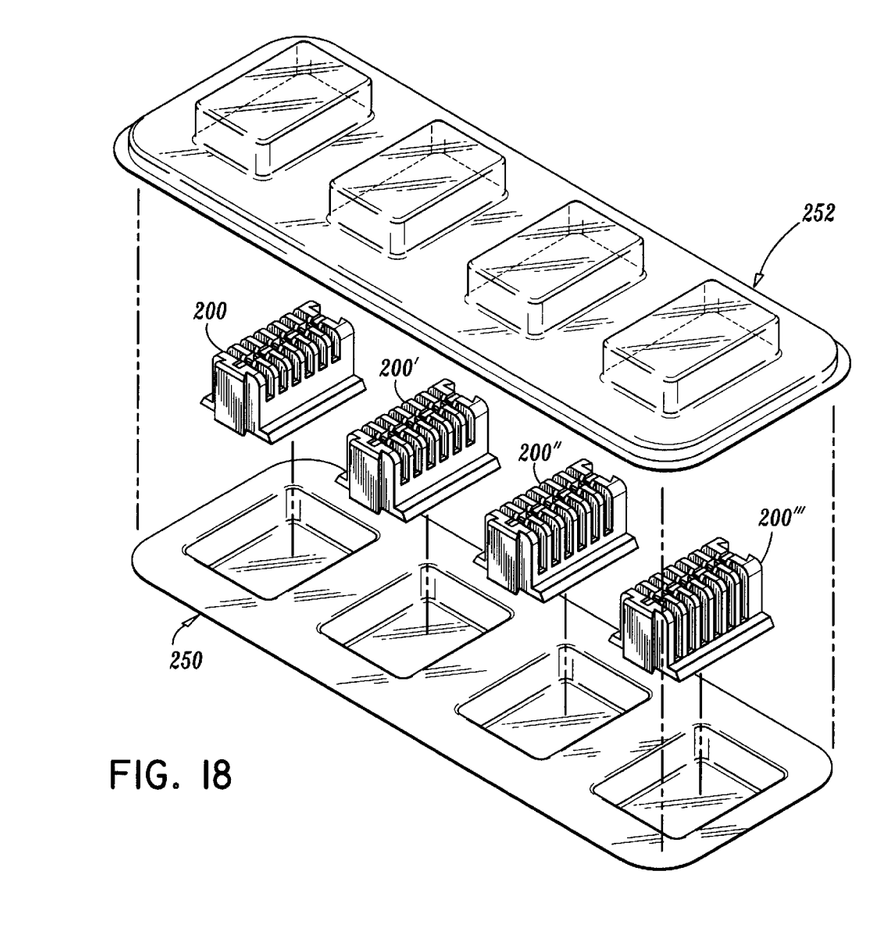
FIG. 18 is a perspective view with parts separated of a surgical kit.

FIG. 18 illustrates a surgical kit shown generally as 240. Kit 240 includes an enclosure having upper and lower halves 250 and 252, respectively. Upper and lower halves 250 and 252 each include a plurality of indentations configured and dimensioned to receive clip cartridges 200, 200', 200" and 200'". Although the kit is shown having four cartridges, kits having more and fewer cartridges are also envisioned. Each cartridge 200, 200', 200" and 200'" include substantially identical external dimensions and an internal dimension or configuration to accommodate small, medium, medium-large or large clip.

Figure 19:
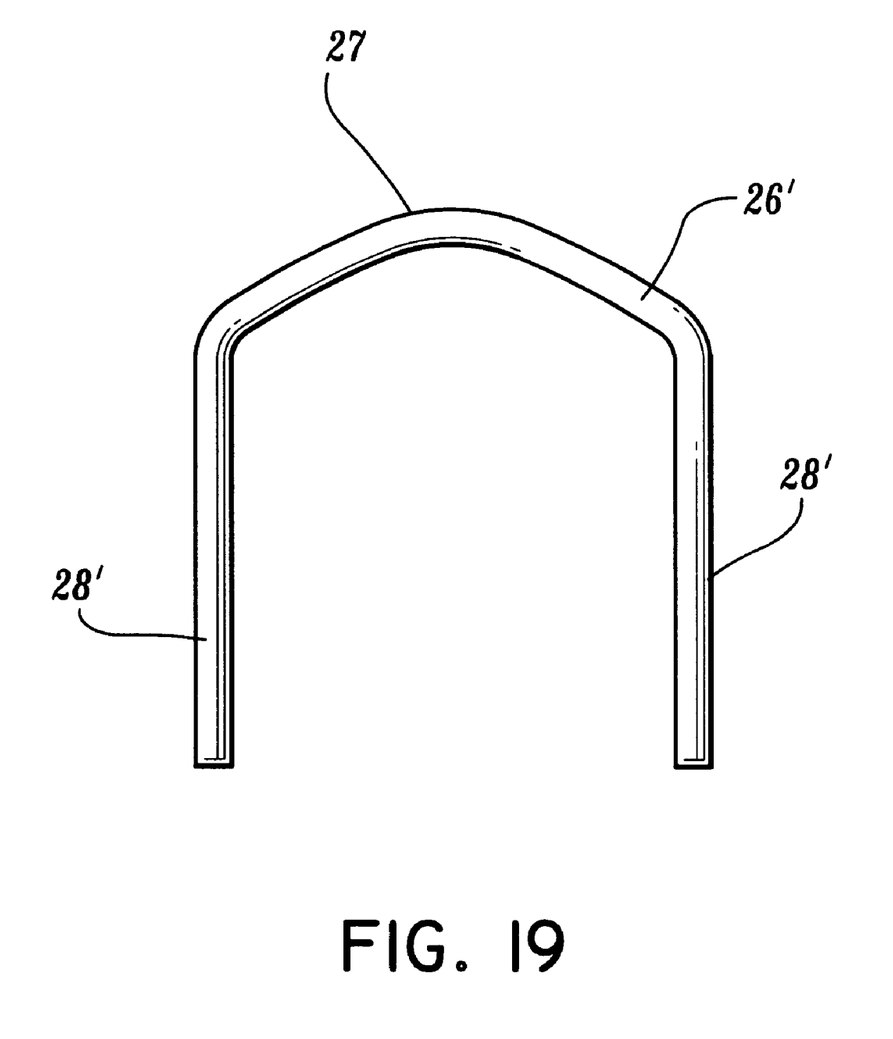
FIG. 19 is a frontal view of an alternate clip design for use with the clip cartridge of FIG. 1.

FIG. 19 illustrates another clip configuration for use in the clip cartridge of FIG. 1. The clip 26' has a substantially rounded crown portion 27 transitioning into legs 28.

It will be understood that various modifications may be made to the embodiments disclosed herein. For example, the shape of the cartridge interlocking structure need not be dovetail-shaped but rather may have any shape which provides the interlocking function. Further, the clip cartridge need not have a base flange to secure the cartridge to a weighted member, but rather may be secured in place by an adhesive positioned on the bottom of the cartridge. Therefore, the above description should not be construed as limiting, but merely as exemplifications of preferred embodiments. Those skilled in the art will envision other modifications within the scope and spirit of the claims appended thereto.

What is claimed is:

1. A clip cartridge for supporting hemostatic clips comprising:
   a body having a base and a plurality of upstanding walls, each of the upstanding walls being spaced from an adjacent upstanding wall to define a hemostatic clip chamber therebetween, each of the clip chambers being configured and dimensioned to receive a clip, at least one of the adjacent upstanding walls including an engagement member positioned to retain the hemostatic clip within the clip chamber; and
   interlocking structure positioned on the body, the interlocking structure being configured to releasably engage interlocking structure on a second clip cartridge to releasably secure two of the cartridges together,
   wherein each upstanding wall includes one of a resilient wall section and a stationary wall section, wherein the upper portion of each clip chamber is defined by one of the resilient wall sections and one of the stationary wall sections.

2. A clip cartridge according to claim 1, wherein the interlocking structure includes a projection formed on one end of the body and a recess formed on the other end of the body.

3. A clip cartridge according to claim 2, wherein the projection and the recess are similarly shaped, the recess being dimensioned to slidably receive the projection.

4. A clip cartridge according to claim 3, wherein the projection and the recess are dovetail-shaped.

5. A clip cartridge according to claim 1, wherein the resilient wall section is positioned to engage a clip during removal of the clip from a respective one of the clip chambers to facilitate removal of the clip from the clip chamber.

6. A clip cartridge according to claim 5, wherein the engagement member includes a rigid projection extending from each stationary wall section into each clip chamber, the rigid projection being positioned across from the resilient wall section and being dimensioned to retain a clip within a respective one of the clip chambers, wherein during removal of a clip from a respective one of the clip chambers, the rigid projection cams the clip into engagement with the resilient wall section to deflect the resilient wall section outwardly.

7. A clip cartridge according to claim 1, further including a base flange positioned on the cartridge, the base flange extending outwardly of the body and being configured to be slidably received in a slot formed in a weighted member.

8. A clip cartridge according to claim 1, further including a pair of supporting members positioned within each of the clip chambers to support a clip thereon.

9. A clip cartridge for supporting hemostatic clips comprising:
   a body having a base and a plurality of upstanding walls, adjacent upstanding walls defining clip chambers configured and dimensioned to receive a hemostatic clip, at least one of the adjacent upstanding walls including an engagement member positioned to retain the hemostatic clip within the clip chamber;
   a projection secured to one end of the body; and
   a recess formed in the other end of the body, the recess being configured and dimensioned to receive the projection to facilitate attachment of two or more clip cartridges together,
   wherein each upstanding wall includes one of a flexible wall section and a stationary wall section, the upper end of each clip chamber being defined by one of the stationary wall sections and one of the flexible wall sections.

10. A clip cartridge according to claim 9, wherein the projection and the recess are dovetail-shaped.

11. A clip cartridge according to claim 9, wherein the engagement member includes a rigid projection extending from each of the stationary wall sections into each of the clip chambers, the rigid projection being positioned to engage and cam a clip into the flexible wall section during removal of the clip from a respective one of the clip chambers.

12. A clip cartridge according to claim 9, further including a pair of supporting members positioned within each of the clip chambers to support a clip thereon.

13. A clip cartridge according to claim 9, further including a base flange secured to the cartridge body, the base flange being configured to be slidably received in a slot formed in cartridge retaining structure.

* * * * *